US011420007B2

(12) United States Patent
Metelits

(10) Patent No.: US 11,420,007 B2
(45) Date of Patent: Aug. 23, 2022

(54) FLOW TRIGGERED GAS DELIVERY

(71) Applicant: EFFORTLESS OXYGEN, LLC, Phoenix, AZ (US)

(72) Inventor: Joel B. Metelits, Scottsdale, AZ (US)

(73) Assignee: EFFORTLESS OXYGEN, LLC, Phoenix, AZ (US)

(*) Notice: Subject to any disclaimer, the term of this patent is extended or adjusted under 35 U.S.C. 154(b) by 0 days.

(21) Appl. No.: 17/393,316

(22) Filed: Aug. 3, 2021

(65) Prior Publication Data
US 2022/0040444 A1 Feb. 10, 2022

Related U.S. Application Data

(63) Continuation-in-part of application No. 17/350,921, filed on Jun. 17, 2021, which is a continuation-in-part of application No. 17/199,172, filed on Mar. 11, 2021, which is a continuation-in-part of application
(Continued)

(51) Int. Cl.
A61M 16/06 (2006.01)
A61M 16/20 (2006.01)
A62B 18/10 (2006.01)
A61M 16/10 (2006.01)
(Continued)

(52) U.S. Cl.
CPC ...... A61M 16/203 (2014.02); A61M 16/0003 (2014.02); A61M 16/0666 (2013.01); A61M 16/0677 (2014.02); A61M 16/104 (2013.01); A61M 16/1005 (2014.02); A62B 18/10 (2013.01); A61M 16/1075 (2013.01); A61M 2016/0018 (2013.01); A61M 2016/0036 (2013.01); A61M 2205/0294 (2013.01);
(Continued)

(58) Field of Classification Search
CPC .. A61M 2016/0015; A61M 2016/0018; A61M 2016/003; A61M 2016/0033; A61M 2016/0036; A61M 2016/0039; A61M 2016/0042; A61M 2016/0024; A61M 16/201; A61M 16/202; A61M 16/204; A61M 16/0069
See application file for complete search history.

(56) References Cited

U.S. PATENT DOCUMENTS 3,906,936 A 9/1975 Habal ........................... 128/2 R
4,278,082 A 7/1981 Blackmer ......... A61M 16/0666
4,567,888 A 2/1986 Robert et al. ............ 128/204.21
(Continued)

FOREIGN PATENT DOCUMENTS

DE 3708146 9/1988 ............ A61M 16/00
DE 19921917 12/2000 ............ A61M 16/00
(Continued)

OTHER PUBLICATIONS

"Sosna et al., Response time of thermal flow sensor with air as fluid, Feb. 26, 2011, Elsevier, Sensors and Actuators A 172 (2011)15-20" (Year: 2011).*
(Continued)

Primary Examiner — Michael J Tsai
(74) Attorney, Agent, or Firm — Hayes Soloway P.C.

(57) ABSTRACT

A fluid delivery system provides fluid, such as supplement oxygen, to a patient in response to inhalation. The fluid delivery system includes a valve assembly that is triggered by sensing onset of inspiration by measuring a change in temperature of air flow in a nasal or oral cannula, mask or helmet.

22 Claims, 10 Drawing Sheets

Related U.S. Application Data

No. 16/986,017, filed on Aug. 5, 2020, now Pat. No. 11,247,008.

(51) Int. Cl.
*A61M 16/00* (2006.01)
*B63C 11/12* (2006.01)

(52) U.S. Cl.
CPC . *A61M 2205/3368* (2013.01); *A61M 2230/42* (2013.01); *B63C 11/12* (2013.01)

(56) References Cited

U.S. PATENT DOCUMENTS

| | | | |
|---|---|---|---|
| 4,612,928 A | 9/1986 | Tiep | 128/204.23 |
| 4,648,395 A | 3/1987 | Sato et al. | 128/204.23 |
| 4,681,099 A | 7/1987 | Sato et al. | 128/204.23 |
| 4,686,974 A | 8/1987 | Sato et al. | 128/204.23 |
| 4,706,644 A | 11/1987 | Nakai | 122/20 |
| 4,706,664 A | 11/1987 | Snook | A61M 16/00 |
| 4,823,788 A | 4/1989 | Smith | 128/205.24 |
| 5,148,802 A | 9/1992 | Sanders et al. | 128/204.18 |
| 5,165,397 A | 11/1992 | Arp | 128/204.21 |
| 5,239,994 A * | 8/1993 | Atkins | A61M 16/0096 |
| | | | 128/204.18 |
| 5,433,193 A | 7/1995 | Sanders et al. | 128/204.18 |
| 5,458,137 A | 10/1995 | Axe et al. | 128/204.23 |
| 5,474,062 A * | 12/1995 | DeVires | A61M 16/204 |
| | | | 128/205.24 |
| 5,485,850 A | 1/1996 | Dietz | 128/204.23 |
| 5,535,738 A * | 7/1996 | Estes | A61M 16/024 |
| | | | 128/204.21 |
| 5,603,315 A | 2/1997 | Sasso | 128/204.18 |
| 5,647,351 A * | 7/1997 | Weismann | A61M 16/024 |
| | | | 128/204.21 |
| 5,694,923 A | 12/1997 | Hete et al. | 128/204.18 |
| 5,803,065 A | 9/1998 | Zdrojkowski et al. | 128/204.23 |
| 5,865,174 A | 2/1999 | Kloeppel | 128/204.23 |
| 5,878,743 A | 3/1999 | Zdrojkowski et al. | 128/204.23 |
| 6,105,575 A | 8/2000 | Estes et al. | 128/204.23 |
| 6,164,276 A | 12/2000 | Bathe | 128/202.22 |
| 6,257,234 B1 | 7/2001 | Sun | 128/204.18 |
| 6,305,374 B1 | 10/2001 | Zdrojkowski et al. | 128/204.21 |
| 6,346,139 B1 | 2/2002 | Czabala | 95/130 |
| 6,532,960 B1 | 3/2003 | Yurko | 128/204.26 |
| 6,544,192 B2 | 4/2003 | Starr et al. | 600/538 |
| 6,581,599 B1* | 6/2003 | Stenzler | A61M 16/203 |
| | | | 128/204.23 |
| 6,609,517 B1 | 8/2003 | Estes et al. | 128/204.23 |
| 6,612,307 B2 | 9/2003 | Byrd | 128/204.26 |
| 6,615,831 B1 | 9/2003 | Truitt et al. | 128/204.18 |
| 6,626,175 B2 | 9/2003 | Jafari et al. | 128/204.21 |
| 6,644,311 B1 | 11/2003 | Truitt et al. | 128/204.22 |
| 6,691,579 B2 | 2/2004 | Orr et al. | 37/700 |
| 6,752,151 B2 | 6/2004 | Hill | 128/204.18 |
| 6,823,866 B2 | 11/2004 | Jafari et al. | 128/204.21 |
| 6,990,980 B2 | 1/2006 | Richey, II | 128/204.26 |
| 7,013,726 B1 | 3/2006 | Drummond et al. | 73/276 |
| 7,013,898 B2 | 3/2006 | Rashad et al. | 128/207.18 |
| 7,066,985 B2 | 6/2006 | Deane et al. | 95/96 |
| 7,135,059 B2 | 11/2006 | Deane et al. | 96/115 |
| 7,152,598 B2 | 12/2006 | Morris et al. | 128/204.23 |
| 7,222,624 B2 | 5/2007 | Rashad et al. | 128/204.23 |
| 7,368,005 B2 | 5/2008 | Bliss | 96/121 |
| 7,438,745 B2 | 10/2008 | Deane et al. | 95/96 |
| 7,585,351 B2 | 9/2009 | Deane et al. | 95/19 |
| 7,621,270 B2 | 11/2009 | Morris et al. | 128/204.23 |
| 7,686,870 B1 | 3/2010 | Deane et al. | 95/115 |
| 7,708,802 B2 | 5/2010 | Deane et al. | 95/19 |
| 7,730,887 B2 | 6/2010 | Deane et al. | 128/205.12 |
| 7,736,132 B2 | 6/2010 | Bliss et al. | 417/273 |
| 7,748,382 B2 | 7/2010 | Denyer et al. | 128/204.21 |
| 7,753,996 B1 | 7/2010 | Deane et al. | 96/130 |
| 7,780,768 B2 | 8/2010 | Taylor et al. | 96/4 |
| 7,841,343 B2 | 11/2010 | Deane et al. | 128/204.23 |
| 7,857,894 B2 | 12/2010 | Taylor et al. | 96/113 |
| 7,866,320 B2 | 1/2011 | Nichols | 128/204.18 |
| 7,922,789 B1 | 4/2011 | Deane et al. | 95/96 |
| 8,070,853 B2 | 12/2011 | Sprinkle | 95/22 |
| 8,142,544 B2 | 3/2012 | Taylor et al. | 95/22 |
| 8,261,742 B2 | 9/2012 | Strothmann et al. | 128/204.23 |
| 8,337,181 B2 | 12/2012 | Orban | 96/121 |
| 8,366,815 B2 | 2/2013 | Taylor et al. | 96/108 |
| 8,398,559 B2 | 3/2013 | Kueck et al. | 600/532 |
| 8,440,004 B2 | 5/2013 | Taylor et al. | 96/121 |
| 8,568,519 B2 | 10/2013 | Taylor et al. | 96/128 |
| 8,607,786 B2 | 12/2013 | Denyer et al. | 128/203.15 |
| 8,640,701 B2 | 2/2014 | Richey, II | 128/204.26 |
| 8,702,841 B2 | 4/2014 | Taylor et al. | 95/25 |
| 9,120,050 B2 | 9/2015 | Richey, II | B01D 53/0476 |
| 9,162,031 B2 | 10/2015 | Gumaste et al. | A61M 15/0091 |
| 9,220,864 B2 | 12/2015 | Taylor et al. | B01D 53/047 |
| 9,229,630 B2 | 1/2016 | Atlas et al. | G06F 3/0488 |
| 9,283,346 B2 | 3/2016 | Taylor et al. | A61M 16/101 |
| 9,375,674 B2 | 6/2016 | Sprinkle et al. | B01D 53/047 |
| 9,592,360 B2 | 3/2017 | Taylor et al. | A61M 16/10 |
| 9,690,300 B2 | 6/2017 | Han et al. | G05D 7/0106 |
| 9,707,366 B2 | 7/2017 | Metelits | A61M 16/0677 |
| 9,724,038 B2 | 8/2017 | Baloa Welzien et al. | A61B 5/4809 |
| 9,737,676 B2 | 8/2017 | Steinhauer et al. | A61M 16/0057 |
| 9,746,359 B2 | 8/2017 | Desilva et al. | G01F 1/50 |
| 9,764,104 B2 | 9/2017 | Gumaste et al. | A61M 15/0091 |
| 9,795,759 B2 | 10/2017 | Barraza et al. | A61M 16/206 |
| 9,821,129 B2 | 11/2017 | Steinhauer et al. | A61M 16/0057 |
| 9,839,760 B2 | 12/2017 | Banassa et al. | A61M 16/205 |
| 9,884,157 B2 | 2/2018 | Weitzel et al. | A61M 15/00 |
| 9,937,305 B2 | 4/2018 | Morrison | A61M 15/0001 |
| 9,956,365 B2 | 5/2018 | Bonassa et al. | A61M 16/00 |
| 9,962,514 B2 | 5/2018 | Williams et al. | A61M 16/202 |
| 9,987,444 B2 | 6/2018 | Colbaugh | A61M 16/0051 |
| 10,004,869 B2 | 6/2018 | Taylor et al. | A61M 16/10 |
| 10,010,696 B2 | 7/2018 | Sprinkle et al. | A61M 16/202 |
| 10,052,048 B2 | 8/2018 | Klewer et al. | A61B 5/113 |
| 10,086,157 B2 | 10/2018 | Kirby et al. | A61M 16/0003 |
| 10,105,099 B2 | 10/2018 | Jaffe et al. | A61B 5/6819 |
| 10,456,536 B2 | 10/2019 | Ven De Laar et al. | A61M 15/0021 |
| 10,527,606 B2 | 1/2020 | Reinstaedtler | G01N 33/497 |
| 10,539,444 B2 | 1/2020 | Desilva et al. | G01F 1/50 |
| 10,561,863 B1 | 2/2020 | Dashevsky et al. | A62B 9/00 |
| 10,646,673 B2 | 5/2020 | Steinhauer et al. | A61M 16/024 |
| 10,646,674 B2 | 5/2020 | Steinhauer et al. | A61M 16/026 |
| 10,695,520 B2 | 6/2020 | Taylor et al. | A61M 16/10 |
| 10,786,179 B2 | 9/2020 | Eschenbacher | A61B 5/097 |
| 10,786,644 B2 | 9/2020 | Taylor et al. | A61M 16/10 |
| 10,792,453 B2 | 10/2020 | Allum | A61M 16/101 |
| 10,821,245 B2 | 11/2020 | Hete et al. | A61M 16/024 |
| 10,828,444 B2 | 11/2020 | Albanese et al. | A61M 16/024 |
| 10,835,700 B2 | 11/2020 | Lunz et al. | A61M 16/0488 |
| 10,859,456 B2 | 12/2020 | Allum | G01L 7/00 |
| 10,863,921 B2 | 12/2020 | Gigi | A61B 5/0816 |
| 10,869,986 B2 | 12/2020 | Taylor et al. | A61M 16/10 |
| 11,083,865 B2 | 8/2021 | Taylor et al. | A61M 16/10 |
| 11,123,512 B2 | 9/2021 | Allum | A61M 16/101 |
| 11,154,256 B2 | 10/2021 | Vissapragada Venkata Satya et al. | A61B 5/7282 |
| 2003/0075179 A1* | 4/2003 | Gale | A61M 16/207 |
| | | | 128/205.24 |
| 2003/0131848 A1 | 7/2003 | Stenzler | 128/204.18 |
| 2003/0140924 A1 | 7/2003 | Aylsworth et al. | 128/204.26 |
| 2003/0145852 A1 | 8/2003 | Schmidt et al. | 128/203.12 |
| 2004/0035422 A1 | 2/2004 | Truitt et al. | 128/204.18 |
| 2004/0221848 A1 | 11/2004 | Hill | 128/204.18 |
| 2005/0033247 A1 | 2/2005 | Thompson | 604/275 |
| 2005/0039752 A1 | 2/2005 | Zaiser | A61M 16/20 |
| 2005/0087190 A1 | 4/2005 | Jafari et al. | 128/204.21 |
| 2005/0092321 A1 | 5/2005 | Aylsworth | |
| 2005/0172966 A1* | 8/2005 | Blaise | A61M 16/204 |
| | | | 128/204.21 |
| 2006/0048781 A1 | 3/2006 | Nawata | 128/204.23 |
| 2006/0086251 A1 | 4/2006 | Sprinkle | 96/96 |

(56) References Cited

U.S. PATENT DOCUMENTS

| | | | |
|---|---|---|---|
| 2006/0169281 A1 | 8/2006 | Aylsworth | 128/204.23 |
| 2006/0207594 A1 | 9/2006 | Stenzler et al. | 128/204.18 |
| 2006/0219245 A1 | 10/2006 | Holder | 128/204.26 |
| 2007/0215156 A1 | 9/2007 | Kwok | 128/204.21 |
| 2007/0221224 A1 | 9/2007 | Pittman et al. | 128/204.22 |
| 2008/0053456 A1* | 3/2008 | Brown | A63B 21/00061 |
| | | | 128/207.16 |
| 2008/0060647 A1 | 3/2008 | Messenger et al. | 128/204.23 |
| 2008/0078384 A1 | 4/2008 | Messenger et al. | 128/203.12 |
| 2008/0078393 A1 | 4/2008 | Acker et al. | 128/204.29 |
| 2008/0196580 A1 | 8/2008 | Bliss et al. | 95/22 |
| 2008/0236584 A1 | 10/2008 | Holder | 128/204.23 |
| 2008/0251079 A1 | 10/2008 | Richey | 128/204.26 |
| 2008/0257145 A1 | 10/2008 | Sprinkle et al. | 95/22 |
| 2009/0145428 A1 | 6/2009 | Sward | 128/202.26 |
| 2009/0199855 A1* | 8/2009 | Davenport | A61M 16/0677 |
| | | | 128/204.23 |
| 2010/0065055 A1 | 3/2010 | Morris et al. | 128/204.22 |
| 2010/0113956 A1* | 5/2010 | Curti | A61M 16/0666 |
| | | | 600/538 |
| 2010/0116270 A1 | 5/2010 | Edwards et al. | 128/201.21 |
| 2011/0301484 A1 | 12/2011 | Curti et al. | A61B 5/08 |
| 2012/0017904 A1 | 1/2012 | Ratto | 128/203.26 |
| 2012/0118291 A1 | 5/2012 | Brodkin | 128/205.23 |
| 2012/0167894 A1 | 7/2012 | O'Leary | 128/207.18 |
| 2013/0092165 A1 | 4/2013 | Wondka | 128/204.25 |
| 2013/0255678 A1 | 10/2013 | Gumaste et al. | A61M 15/0065 |
| 2014/0150792 A1 | 6/2014 | Christopher et al. | |
| | | | A61M 16/0051 |
| 2014/0261414 A1 | 9/2014 | Weitzel | A61M 15/0051 |
| 2014/0275857 A1 | 9/2014 | Toth | A61B 5/083 |
| 2015/0059764 A1 | 3/2015 | Metelits | A61M 16/0677 |
| 2015/0090261 A1 | 4/2015 | Crosbie | 128/203.14 |
| 2015/0173419 A1 | 6/2015 | Tu | A24F 40/46 |
| 2016/0166797 A1 | 6/2016 | Orr | A61M 16/0666 |
| 2016/0354573 A1 | 12/2016 | Buswell | A61M 16/024 |
| 2016/0367779 A1 | 12/2016 | Landis et al. | A61M 16/0666 |
| 2017/0368275 A1 | 12/2017 | Gumaste et al. | A61M 15/0065 |
| 2018/0085544 A1 | 3/2018 | Holyoake et al. | A61M 16/024 |
| 2019/0060591 A1 | 2/2019 | Kertser | A61M 16/0841 |

FOREIGN PATENT DOCUMENTS

| | | | |
|---|---|---|---|
| EP | 0385250 | 9/1990 | A61M 15/00 |
| WO | WO2008092021 | 7/2008 | A61M 16/04 |
| WO | WO2013043504 | 3/2013 | A62B 9/02 |
| WO | WO-2013070545 A1 * | 5/2013 | A61B 5/083 |
| WO | WO2019119054 | 6/2019 | A61M 16/10 |

OTHER PUBLICATIONS

Vraanes et al., Thermal Mass flow sensors for gas and Liquid applications, Nov. 15, 2017, Renesas, White papers. (Year: 2017) (Year: 2017).*

Australian Examination Report issued in Australian Patent Application Serial No. 2014315301, dated Jul. 21, 2017 (3 pages).

Australian Notice of Acceptance for Patent Application issued in Australian Patent Application Serial No. 2014315301, dated Sep. 13, 2017 (3 pages).

Chinese Official Action issued in Chinese Patent Application Serial No. 201480049058.3, dated Oct. 8, 2019 (7 pages).

Chinese Official Action issued in Chinese Patent Application Serial No. 201480049058.3, dated Sep. 27, 2018 (8 pages).

Chinese Official Action issued in Chinese Patent Application Serial No. 201480049058.3, dated Mar. 13, 2019 (7 pages).

European Office Action issued in application No. 14842330.0, dated Jul. 30, 2019 (6 pgs).

European Office Action issued in application No. 14842330.0, dated Jun. 4, 2018 (5 pgs).

European Office Action issued in application 14842330.4, dated Apr. 8, 2020 (5 pgs).

European Search Report issued in application 14842330.4, dated Mar. 29, 2017 (7 pgs).

Indonesia Office Action issued in application P00201602039, dated Jun. 20, 2019 (4 pgs).

India Office Action issued in application 201627010165, dated Dec. 16, 2019 (8 pgs).

International Preliminary Report on Patentability issued in corresponding PCT patent Appln. No. PCT/US2012/055514 dated Mar. 25, 2014 (6 pgs).

International Search Report issued in corresponding PCT patent Appln. No. PCT/US2012/055514 dated Jan. 25, 2013 (9 pgs).

International Preliminary Report on Patentability issued in related application No. PCT/US14/53924, dated Mar. 17, 2016 (7 pgs).

International Search Report and Written Opinion issued in related application No. PCT/US14/53924, dated Jan. 2, 2015 (9 pgs).

Japanese Office Action issued in application No. 2016-540352, dated Jan. 19, 2018 with English translation (7 pgs).

Japanese Office Action issued in application No. 2016-540352, dated Jun. 29, 2018 with English translation (4 pgs).

Philippines Office Action issued in application No. 500423, dated Mar. 1, 2018 (2 pgs).

Russian Office Action issued in application No. 2016107490, dated March 20, 2018 with English translation (15 pgs)

Russian Decision to Grant issued in application No. 2016107490, dated Jun. 13, 2018 with English translation (18 pgs).

Palwai, A. et al. "Critical Comparisons of the Clinical Performance of Oxygen-conserving Devices" *American Journal of Respiratory Critical Care Medicine* 181(10): 1061-1071 May 15, 2010 (25 pgs).

Official Action issued in corresponding U.S. Appl. No. 14/476,552, dated Feb. 2, 2017 (30 pgs).

Official Action issued in corresponding U.S. Appl. No. 16/986,017, dated Mar. 31, 2021 (28 pgs).

Official Action issued in corresponding U.S. Appl. No. 16/986,017, dated Jul. 7, 2021 (21 pgs).

U.S. Appl. No. 16/986,017, filed Aug. 5, 2020.

U.S. Appl. No. 17/199,172, filed Mar. 11, 2021.

U.S. Appl. No. 17/350,921, filed Jun. 17, 2021.

U.S. Appl. No. 16/986,017, filed Aug. 5, 2020, Metelits.

U.S. Appl. No. 17/199,172, filed Mar. 11, 2021, Metelits.

U.S. Appl. No. 17/350,921, filed Jun. 17, 2021, Metelits.

Hedrich et al., Thermal flow sensors for MEMS spirometric devices, Mar. 18, 2020, Elsevier, Sensors and Actuators A 162 (2010) 373-378, 2010.

Sosna et al., Response time of thermal flow sensor with air as fluid, Feb. 26, 2011, Elsevier, Sensors and Actuators A 172 (2011, 15-20), 2011.

Vraanes et al., Thermal Mass flow sensors for gas and liquid applications, Nov. 15, 2017, Renesas, White Papers, 2017.

Official Action issued in related U.S. Appl. No. 17/350,921, dated Nov. 9, 2021, 51 pages.

International Search Report and Written Opinion issued in PCT International Patent Application Serial No. PCT/US21/44473, dated Nov. 8, 2021 (10 pages).

Notice of Allowance issued in related U.S. Appl. No. 16/986,017, dated Nov. 18, 2021, 19 pages.

* cited by examiner

Table 1

| Sensory Type | Trigger Pressure (Pascal) |
|---|---|
| Temperature Sensor Flow Sensor per the Disclosure | 0.3 |
| Chad Lotus Model OM-700 Pressure Sensor | 12.1 |
| SmartDose Model CTOX-MN02 Pressure Sensor | 15.7 |

FIG. 5

FLOW TRIGGERED GAS DELIVERY

CROSS REFERENCE TO RELATED APPLICATIONS

This application is a continuation-in-part (CIP) of my co-pending U.S. patent application Ser. No. 17/350,921, filed Jun. 17, 2021, which in turn is a continuation-in-part (CIP) of my co-pending U.S. patent application Ser. No. 17/199,172 filed Mar. 11, 2021, which application in turn is a continuation-in-part (CIP) of my co-pending U.S. patent application Ser. No. 16/986,017, filed Aug. 5, 2020, the contents of which are incorporated herein by reference.

BACKGROUND OF THE DISCLOSURE

The present disclosure relates to devices and methods for monitoring and delivering oxygen or other gas to a human or other animal, and for effectively conserving the delivery of said gas. The disclosure has particular utility for delivery of supplemental oxygen to a human or animal patient and will be described in connection with such utility, although other utilities are contemplated.

In the U.S. today well over 1.5 million human patients are receiving supplemental oxygen therapy at a cost believed to be excess of 2 billion dollars annually. Moreover, acute cases due to COVID-19 have exacerbated the demand for supplemental oxygen to a point where some hospitals are running out of oxygen supplies.

Most of the patients receiving long term supplemental oxygen therapy (LTOT) suffer from chronic hypoxemia as a result of having a chronic obstructive pulmonary disease (COPD). Presently there is no cure for this condition. However the detrimental impact of chronic hypoxemia may be mitigated by the administration of long term oxygen therapy (LTOT). The continuous inhalation of low flows of oxygen, typically 2-3 lpm (liter per minute), from a nasal cannula increases the concentration of oxygen that the patient is breathing. It is estimated that for each 1 lpm flow, the overall inhaled concentration rises by 3-4%. The increase in oxygen concentration compensates for the poor function of the patient's lungs in absorbing oxygen.

Generally when a patient is diagnosed with chronic hypoxemia, oxygen is prescribed at a fixed flow rate based on a 20-minute titration test in the doctor's office. During the test, the patient's blood oxygen saturation is measured by either using an invasive blood gas analyzer or a non-invasive device such as a pulse oximeter. While measuring the blood saturation ($SpO_2$), the patient may be asked to walk on a treadmill so as to measure his or her need for supplemental oxygen while exerting him or herself. Based on this brief test, a fixed flow of supplemental oxygen is prescribed. The patient may be advised to increase the flow rate of supplemental oxygen during exertion, for example, while climbing stairs, while sleeping or if they feel short of breath. The patient will need confirmation of the adequacy of supplemental oxygen treatment, with the goal of keeping the patient's oxygen saturation above 90% during all of their activities, including during sleep. Some patients may be prescribed supplemental oxygen to breathe 24 hours per day or may only require supplemental oxygen while ambulating or may need supplemental oxygen treatment only when sleeping. Among patients requiring LTOT during their waking hours, often higher flow rates are required while sleeping. It is common practice to increase the flow rate by 1 liter per min while a patient is sleeping.

If a patient needs to breathe supplemental oxygen even while resting, he or she will be given a stationary oxygen generating unit in his or her home which can be set to produce, e.g., up to 5 liters per minute of 93% oxygen. Generally, the units today are manually set to a prescribed flow rate in liters per minute. If a patient requires supplemental oxygen while ambulating, he or she typically will carry small high pressure oxygen cylinders or small refillable liquid oxygen dewars. Small portable oxygen generators are also available which can produce up to 3 liters per minute of continuous oxygen or deliver pulsed oxygen at higher flow rates. These portable oxygen delivery systems all have drawbacks. Portable concentrators are usually bulkier and noisier and have a relatively short battery life. The small high pressure oxygen cylinders have restricted capacity, especially the smaller ones, but do not need a battery or make the kind of noise produced by the concentrators.

Due to the expense of providing oxygen in small cylinders and dewars for ambulation, various oxygen conserving devices have been developed to conserve the oxygen flow. These prior art oxygen conserving devices only deliver short pulses of oxygen at the beginning of a patient's inhalation. By not delivering oxygen during exhalation or the later period of inhalation, the oxygen which would have had no impact on increasing the patient's oxygen saturation is conserved. There now exists both pneumatic and electronic oxygen conserving devices which claim to achieve oxygen conserving ratios from 2:1 to 7:1 compared to the delivery of continuous oxygen flow. Such higher conservation ratios are achieved by the electronic devices which are programmed to skip breaths so that oxygen pulse is only delivered every other breath. However, electronic devices cannot be used on all ambulating patients since such high conservation ratios can actually result in poor oxygen saturation for the patient particularly during periods of increased oxygen utilization as in walking vigorously or walking up stairs.

Moreover, currently available conserving devices measure a drop in nasal air pressure, which for many patients is inadequate to trigger the release of oxygen under various circumstances, including: extremely reduced respiratory function; most mouth breathing; talking while walking; while walking briskly or while talking intensely; or while sleeping. Upon initiation of these ambulatory devices, patients are "taught" to focus on nasal breathing to help trigger the device. Often a patient needs to stop his or her activity and focus on his or her nasal breathing, or to put the nasal cannula probe in his or her mouth to more effectively trigger the device.

Pressure sensing of the onset of inhalation in electronic oxygen conservers is currently is accomplished in one of two ways:

1. Some prior art designs employ a dual lumen cannula in which one of the lumens is dedicated to pressure sensing while the other is dedicated to the supply of oxygen. This design is meant to be more sensitive to the onset of inhalation but suffers from the drawback of only being able to deliver oxygen to one of the nasal passages.

2. Other designs use a single lumen cannula that typically has a pressure sensor connected to a T piece below two nasal prongs. Overall pressure drop associated from inhalation is sensed from both nasal passages and oxygen is then delivered to both nasal passages.

Both designs suffer from a delay in triggering a flow of oxygen due to the hysteresis which is inherent in pressure sensing. However, even a slight delay in triggering a flow of oxygen is readily perceived by the patient. Another drawback of current designs using pressure sensors is that if one of the patient's nasal passages is blocked, it will interfere with the detection and delivery of oxygen.

Yet another flaw with current oxygen generating systems is the fact that a patient's ideal need for oxygen varies with time both in the short term as a result of varying exertion and in the long term as a result of improvement or deterioration in health. When a doctor prescribes a fixed flow rate of oxygen for a patient, the doctor is mainly concerned with ensuring that the patient's blood saturation does not drop below an oxygen saturation of 88-89%. The doctor does not want to have a patient experience desaturation of oxygen below 90% during any of the patient's activities. Although there exist theoretical concerns about potential toxicities in patients administered oxygen in high concentrations (above 50 percent) for extended time periods (e.g., absorptive atelectasis, increased oxidative stress, and inflammation), clinical experience has provided little support for these concerns in the setting of LTOT. ("Long-term supplemental oxygen therapy." *Up-To-Date*; Jan. 18, 2013. Brian L Tiep, M D Rick Carter, PhD, MBA).

Current oxygen treatment plans are prone to error as reported by a study by Fussell et al. (*Respiratory Care*. February 2003, Vol. 48 No. 2). In that study, blood saturation levels of 20 patients suffering from COPD were monitored continuously using pulse oximetry to confirm if each patient's oxygen prescription adequately maintained his or her saturation. The conclusion of the study was that there was a poor relationship between conventional oxygenation assessment methods and continuous ambulatory oximetry during LTOT screening with COPD patients. More recently in an article entitled "Critical Comparisons of the Clinical Performance of Oxygen-conserving Devices," Am. J. Respir. Crit. Care Med. 2010 May 15; 181(10): 1061-1071, the current collection of conserving devices all based on pressure sensing were criticized as failing to deliver on their efficacy claims. The authors claimed that "Although each device activated during nose and mouth breathing, none consistently performed according to engineering expectations."

When a patient obtains low oxygen saturation results while using conserving devices or fixed oxygen flow rates, the natural response is to simply increase the flow rate, when in actuality, low oxygen saturation results often are caused by a delay in triggering supplemental oxygen flow as early as possible at onset of inhalation. Increased nasal flow rates become increasingly expensive and are generally not well tolerated. Some COPD patients who use stationary oxygen concentrators in their homes are financially impaired and are concerned about the power costs of continuously running an oxygen concentrator. In many cases this has led to a compliance issue where the patient may elect to not switch on the concentrator and follow the therapy as prescribed by the doctor in order to save on their electricity bill. Moreover, these oxygen concentrators throw a fair amount of heat into the room, which may further add to energy costs, i.e., for cooling the room. Current oxygen concentrator designs typically will produce a maximum flow rate, e.g., of 5 liters per minute. If a patient's resting prescription is 2 liters per minute, the patient may set a flow rate through their cannula to the required flow and the excess oxygen that is being produced is simply pushed into the nostrils which while mouth breathing may be wasted. Many oxygen therapy patients can spend a significant amount of their time while active, or talking, or napping, or sleeping with blood oxygen saturation levels that are unacceptable.

Current pressure-based oxygen conserving units fail to live up to their claims when a patient is mouth breathing during more vigorous activity, while talking, while eating and/or when sleeping. Often patients on ambulatory oxygen will have to stop and focus on their nose breathing, or put the nasal cannula prongs in their mouth and suck on them to trigger the release of oxygen. When oxygen needs are not being met, the simple solution is to increase the nasal flow rate, which causes increasing problems of uncomfortable nasal passage drying and sometimes nasal mucosal bleeding. Further, patients often stop their oxygen delivery system altogether when eating.

In my prior U.S. Pat. No. 9,707,366, I describe an improved system, method and apparatus for controlled delivery of oxygen to patient in which a nasal cannula or a combined nasal and oral cannula with a valve assembly and a flow sensor for sensing "flow leakage" through a patient's nasal cavity, while they are breathing. This "hidden signal," coupled with simultaneous monitoring of nasal and/or oral flow patterns, enables an on-demand oxygen delivery system without uncertainty or misdirected oxygen—both of which lead to oxygen wastage, or inadequate oxygen delivery to the patient. More particularly, my prior '366 patent describes a fluid delivery system comprising at least one source of fluid; at least one valve assembly coupled to said at least one source of fluid, wherein the at least one valve assembly is configured to allow flow of fluid from the at least one source during patient inspiration; an outlet end comprising a nasal or oral cannula in fluid communication with the at least one valve assembly; and a nasal flow sensor for triggering fluid delivery in response to patient inspiration. The fluid delivery system further including a power source configured to operate the at least one valve assembly. The location of the nasal flow sensor may be in or adjacent the nasal cannula or oral cannula, adjacent the fluid source, or in air tubing between the nasal cannula or oral cannula and the at least one source of fluid.

SUMMARY OF THE DISCLOSURE

The present disclosure provides improvements over the method and apparatus of my prior '366 patent by providing an improved trigger mechanism for triggering the valve to release fluid from the fluid source for delivery to the patient via the nasal or oral cannula. The fluid delivered by the method may comprise oxygen. More particularly, the present disclosure in one aspect provides a flow sensor that employs heater(s) and temperature sensor(s) to detect onset of inspiration by measuring a temperature differential caused by the convective cooling induced by the flow of the fluid, and trigger flow within less than about 20 milliseconds, typically within 10-20 milliseconds of the onset of inspiration, which is far better than any currently available pressure sensor is capable of providing.

Also, to permit the use of a high sensitivity air flow sensor, to protect the sensor from high pressure oxygen flow, the present disclosure preferably isolates the air flow sensor from the oxygen flow line via a switching valve.

In one aspect of the disclosure there is provided a fluid delivery system for controlling delivery of a fluid to a human or animal comprising at least one source of said fluid; at least one valve assembly coupled to said at least one source of said fluid, wherein the at least one valve assembly is configured to allow flow of said fluid from the at least one source during said human or animal inspiration; an outlet end comprising a nasal or oral cannula in fluid communication with the at least one valve assembly; and a flow sensor for triggering fluid delivery in response to said human or animal inspiration, wherein the flow sensor is in fluid communication with and upstream the nasal or oral cannula, and includes a temperature sensor such as a thermistor configured to detect a change in temperature indicative of onset of inspiration by said human or animal, within less than about 20 milliseconds, typically within 10-20 milliseconds of said onset of inspiration. The system also may include a power source configured to operate the at least one valve assembly.

In another aspect of the disclosure the flow sensor is located in or adjacent the nasal cannula or oral cannula, or is located in tubing connective the nasal cannula or oral cannula and the at least one source of said fluid. The nasal and the oral cannula may be coupled to one another. Preferably, the fluid delivered preferably comprises supplemental oxygen, a therapeutic gas or an anesthetic gas.

In one embodiment the fluid delivery system comprises electronic circuitry for controlling the at least one valve assembly based on signals from the flow sensor. Preferably, the electronic circuitry comprises a trigger mechanism for actuating the release of said fluid through said at least one valve assembly.

The fluid delivery system may also comprise a heater configured to heat the flow sensor or the fluid upstream of the flow sensor to above ambient.

In a preferred embodiment the temperature sensor is configured to detect the onset of inspiration and the onset of exhalation by a directional change of temperature, and wherein the system optionally includes heaters located upstream and optionally downstream of said temperature sensor.

In another embodiment the flow sensor is isolated from the at least one source of said fluid by a piezo actuator valve.

The present disclosure also provides an apparatus for conserving fluid being delivered from a fluid supply to a human or animal comprising: a fluid conserver controller connected between the fluid supply and a nasal cannula or an oral cannula, wherein said controller comprises at least one valve triggered selectively to deliver said fluid to the nasal or oral cannula; a flow sensor configured to sense inspiration by human or animal; and a trigger mechanism, communicating with said sensor for actuating the conserver controller, wherein the flow sensor is in fluid communication with said nasal or oral cannula, and includes a temperature sensor such as a thermistor configured to detect a change in temperature indicative of onset of said inspiration by said human or animal, within less than about 20 milliseconds, typically within 10-20 milliseconds of said onset of inspiration.

In one embodiment of the disclosure the flow sensor and trigger mechanism are remote from one another, and the flow sensor and the trigger mechanism communicate either by wire or wirelessly.

In a preferred embodiment of the disclosure, the flow sensor and trigger mechanism are remote from one another, and the flow sensor and the trigger mechanism communicate either by wire or wirelessly.

In a preferred embodiment of the disclosure the at least one valve comprises at least one valve, and the fluid supply preferably comprises oxygen, a therapeutic gas or an anesthetic gas.

In one embodiment, the apparatus further comprises electric circuitry for controlling the at least one valve based on signals from the flow sensor, and/or a heater configured to heat the flow sensor or the fluid upstream of the flow sensor to above ambient.

In one embodiment the temperature sensor is configured to detect the onset of inspiration and the onset of exhalation by a directional change of temperature, and wherein the system optionally includes heaters located upstream and optionally downstream of said temperature sensor.

In another embodiment the flow sensor is isolated from the fluid supply by a piezo actuator valve.

The present disclosure also provides a method for conserving delivery of a fluid from said fluid source to a patient, comprising the steps of: providing a valve in communication with a fluid source and a nasal or oral nasal cannula worn by the patient; sensing, with a flow sensor including a temperature sensor such as a thermistor in communication with the nasal or oral cannula, onset of inspiration by detecting a change in temperature of airflow through said nasal or oral cannula, within not more than about 15-20 milliseconds of said onset of inspiration, triggering the valve, in response to the sensed onset of inspiration to release said fluid from the fluid source for delivery to the patient via the nasal or oral nasal cannula preferably the fluid comprises oxygen, a therapeutic gas of an anesthetic gas.

In one embodiment the method comprises heating the flow sensor or the fluid upstream of the flow sensor to above ambient.

In another embodiment the flow sensor comprises a temperature sensor configured to detect the onset of inspiration and onset of exhalation by directional change of temperature.

In yet another embodiment the method includes the step of isolating the flow sensor from the fluid source while sensing onset of inspiration.

The present disclosure also provides a fluid delivery system for controlling delivery of a fluid to a human or animal comprising:

at least one source of said fluid;

at least one valve assembly coupled to said at least one source of said fluid, wherein the at least one valve assembly is configured to allow flow of said fluid from the at least one source during said human or animal inspiration;

an outlet end comprising a nasal or oral cannula, mask or helmet in fluid communication with the at least one valve assembly; and a flow sensor for triggering fluid delivery in response to said human or animal inspiration, wherein the flow sensor is in fluid communication with and upstream the nasal or oral cannula, mask or helmet and comprises a temperature sensor configured to detect a change in temperature indicative of onset of inspiration by said human or animal, within less than about 20 milliseconds, preferably 10-20 milliseconds, of said onset of inspiration, and wherein the at least one valve assembly is configured to ramp fluid flow delivery to coordinate with a breathing pattern of the human or animal.

In one embodiment the fluid delivery system comprises a power source configured to operate the at least one valve assembly.

In another embodiment the flow sensor is located in or adjacent the nasal cannula or oral cannula, mask or helmet or is located in tubing connective the nasal cannula, mask or helmet or oral cannula and the at least one source of said fluid.

In yet another embodiment the nasal and the oral cannula are coupled to each other.

In still yet another embodiment the fluid delivered comprises supplemental oxygen, a therapeutic gas or an anesthetic gas.

In a fourth embodiment, the fluid delivery system comprising electronic circuitry for controlling the at least one valve assembly based on signals from the flow sensor, and the electronic circuitry preferably comprises a trigger mechanism for actuating the release of said fluid through said at least one valve assembly.

In a particularly preferred embodiment, the at least one valve assembly is configured to ramp fluid flow from a starting flow of 15-40%, preferably 20-35%, more preferably about 33% from triggering to 100% flow at inspiratory capacity of the human or animal.

In another embodiment the fluid delivery system further comprises a heater configured to heat the flow sensor or the fluid upstream of the flow sensor to above ambient, and, if desired the temperature sensor is configured to detect the onset of inspiration and the onset of exhalation by a directional change of temperature, and wherein the system optionally includes heaters located upstream and optionally downstream of said temperature sensor.

In another embodiment the flow sensor is isolated from the at least one source of said fluid by a piezo actuator valve.

The present disclosure also provides an apparatus for conserving fluid being delivered from a fluid supply to a human or animal comprising:

a fluid conserver controller connected between the fluid supply and a nasal cannula or an oral cannula, mask or helmet wherein said controller comprises at least one valve triggered selectively to deliver said fluid to the nasal or oral cannula, mask or helmet;

a flow sensor configured to sense inspiration by human or animal; and a trigger mechanism, communicating with said flow sensor for actuating the conserver controller, wherein the flow sensor is in fluid communication with said nasal or oral cannula, mask or helmet, and includes a temperature sensor configured to detect a change in temperature indicative of onset of said inspiration by said human or animal, within less than about 20 milliseconds, preferably 10-20 milliseconds, of said onset of inspiration, wherein the at least one valve assembly is configured to ramp fluid flow delivery to coordinate with a breathing pattern of the human or animal.

In one embodiment of the apparatus, the flow sensor and said trigger mechanism are remote from one another, and wherein said flow sensor and said trigger mechanism communicate either by wire or wirelessly.

In a further embodiment of the apparatus the fluid supply comprises oxygen, a therapeutic gas or an anesthetic gas.

In a preferred embodiment the apparatus further comprises electric circuitry for controlling the at least one valve based on signals from the flow sensor, and optionally further comprising a heater configured to heat the flow sensor or the fluid upstream of the flow sensor to above ambient.

In a particularly preferred embodiment the at least one valve assembly is configured to ramp fluid flow from a starting flow of 15-40%, preferably 20-35%, more preferably about 33% from triggering to 100% flow at inspiratory capacity of the human or animal.

In yet another embodiment of the apparatus the temperature sensor is configured to detect the onset of inspiration and the onset of exhalation by a directional change of temperature, and wherein the system optionally includes heaters located upstream and optionally downstream of said temperature sensor.

In still yet another apparatus the flow sensor is isolated from the fluid supply by a piezo actuator valve.

The present disclosure also provides a method for conserving delivery of a fluid from a fluid source to a patient, comprising the steps of:

providing a valve in communication with a said fluid source and a nasal or oral nasal cannula, mask or helmet worn by the patient;

sensing, with a flow sensor in communication with the nasal or oral cannula, mask or helmet, onset of inspiration by detecting a change in temperature of fluid through said nasal or oral cannula, mask or helmet within less than about 20 milliseconds, preferably 10-20 milliseconds of said onset of inspiration, and triggering the valve, in response to the sensed onset of inspiration to release said fluid from the fluid source for delivery to the patient via the nasal or oral nasal cannula, mask or helmet, wherein the valve assembly is configured to ramp fluid flow delivery to coordinate with a breathing pattern of the human or animal.

In a preferred embodiment of the method the fluid comprises oxygen, a therapeutic gas of an anesthetic gas, and optionally, further comprising heating the flow sensor or the fluid upstream of the flow sensor to above ambient.

In another embodiment of the method the flow sensor comprises a temperature sensor configured to detect the onset of inspiration and onset of exhalation by directional change of temperature.

Yet another embodiment of the method includes the step of isolating the flow sensor from the fluid source while sensing onset of inspiration.

In still another embodiment of the method, the valve assembly is configured to ramp fluid flow from a starting flow of 15-40%, preferably 20-35%, more preferably about 33% from triggering to 100% flow at inspiratory capacity of the human or animal.

BRIEF DESCRIPTION OF THE DRAWINGS

The disclosure will be better understood from a reading of the following detailed description taken in conjunction with the drawings in which like reference designators are used to designate like elements, and in which:

FIG. 5 is a table comparing the onset of gas flow delivery by the system of the present disclosure with conventional prior art systems employing pressure flow sensors;

DETAILED DESCRIPTION OF THE DISCLOSURE

Figure 1:
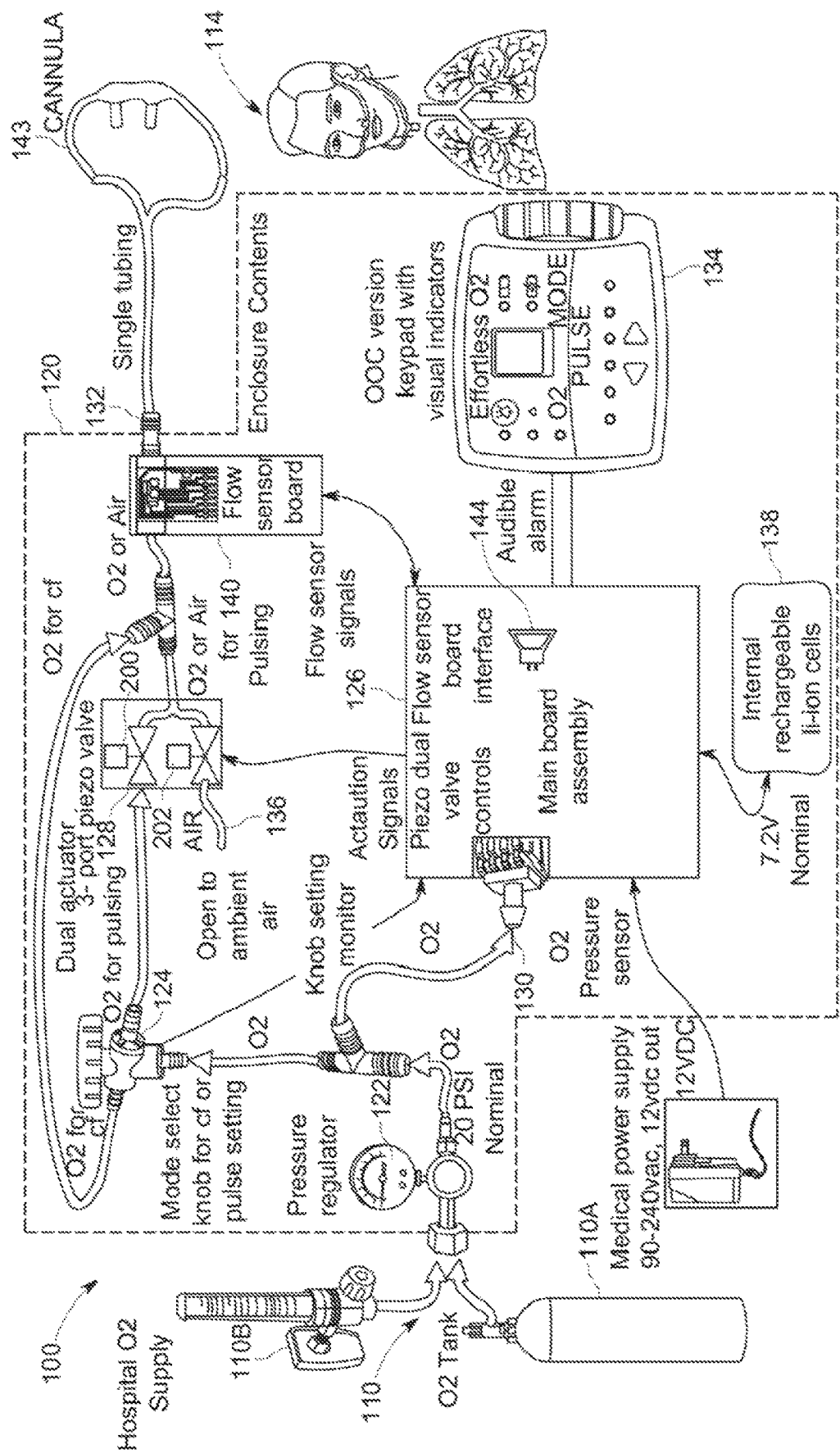
FIGS. 1 and 2 are block diagrams of two different systems for fluid delivery in accordance with the present disclosure.

As used herein "nasal cannula" is intended to include two lumen nasal cannula as well as nasal masks or pillow masks. And "oral cannula" is intended to include face masks as well as breathing tubes, mouth pieces and the like, as well as diver and hazard helmets and the like.

Embodiments are described in the following description with reference to the drawing figures in which like numbers represent the same or similar elements. Reference throughout this specification to "one embodiment," "an embodiment," "certain embodiments," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment.

The described features, structures, or characteristics of the disclosure may be combined in any suitable manner in one or more embodiments. In the following description, numerous specific details are recited to provide a thorough understanding of embodiments of the disclosure. One skilled in the relevant art will recognize, however, that the disclosure may be practiced without one or more of the specific details, or with other methods, components, materials, and so forth. In other instances, well-known structures, materials, or operations are not shown or described in detail to avoid obscuring aspects of the disclosure.

The fluid delivery system of the present disclosure provides supplemental oxygen, to a human or animal in intermittent time intervals, based on the patient's tidal breathing. The fluid delivery system includes a nasal or oral nasal flow-triggered valve assembly that opens in response to a patient's inhalation, and closes during the inspiratory phase to conserve oxygen which would otherwise be wasted on filling up a patient's "dead space" prior to the end of inhalation. That is to say, the present disclosure senses onset of inspiration, through a temperature sensor placed in a nasal cannula or oral cannula, or supply tube in the case of a helmet, and triggers the regulator valve to open upon onset of inhalation, i.e., within not more than about 15-20 milliseconds of onset of inhalation, and to remain open for a period of time consistent with the human or animal's tidal breathing.

The nasal or oral flow temperature sensor is sensitive enough to sense onset of inspiration within less than about within 20 milliseconds, typically within 10-20 milliseconds, and send a signal to the valve assembly to open and permit flow of oxygen for a period of time. By opening within not more than about 20 milliseconds, typically within 10-20 milliseconds after onset of inspiration, and then staying open for a limited period of time, it is possible to achieve a truly on-demand oxygen delivery system without uncertainty or misdirected oxygen—both of which lead to oxygen wastage or inadequate oxygen delivery to the patient. With onset of inspiration flow information, the waste involved, for example, with pulse regulated oxygen or continuous flow oxygen is eliminated. Moreover, the patient or user has a pleasing sense of synchrony between breath initiation and delivery of oxygen and, by eliminating any perceptible delay in oxygen delivery, feels free to move about and talk spontaneously without fear of missing his or her oxygen pulse. Also the efficiency of conserving devices can be utilized in hospitalized or bedridden patients from a central liquid supply with a reliable pulse oxygen delivery system.

Moreover, unlike pressure flow sensors described in the prior art, sensing and thus triggering using a temperature sensor in accordance with my disclosure is essentially instantaneous, i.e., within less than about 20 milliseconds, typically within 10-20 milliseconds of onset of inhalation. Thus, there is essentially no delay delivering supplemental oxygen. Nor is there any waste of oxygen compared to conventional pressure flow-sensor detectors. Consequently, the flow of supplemental oxygen is turned on essentially with onset of inhalation, and timed to remain on for a period of time in concert with the ramp up of the patient's tidal breathing and/or upon detection of the onset of exhalation. As a result, supplemental oxygen is conserved because the supplemental oxygen is not provided when the patient does not need the oxygen: during the filling of "dead space" (i.e., the volume of air which is inhaled that does not take part in the gas exchange), or during exhalation.

As used herein, inhalation is used synonymously with inspiration, and exhalation is used synonymously with expiration. Inhalation is the movement of air from the external environment, through the airways, and into the lungs. During inhalation, the chest expands and the diaphragm contracts downwardly or caudally, resulting in expansion of the intrapleural space and a negative pressure within the chest cavity. This negative pressure results in airflow primarily from either the nose or the mouth into the pharynx (throat) and trachea, eventually entering the lungs. By using a flow sensor in the form of a temperature sensor, the determination of onset of inspiration is essentially instantaneous, i.e., within less than about 20 milliseconds, typically within 10-20 milliseconds of onset of inspiration taking advantage of the most important phase of inspiration to deliver supplemental oxygen. Although any bolused or pulsed oxygen delivery system is set as a flow rate equivalent, there is more consistency and parity with bolus amounts and continuous flow rates. The term "pulse equivalent" which is presumed comparable to continuous flow is how current conserving regulators are set. Continuous flow rates are set at liters per minute.

Since pulse units do not put out continuous oxygen, they cannot be measured in liters per minute. Instead, they are classified by size of the individual pulse (bolus), i.e., how often that pulse can be delivered in a minute, and when the pulse is delivered in the inspiratory (breathing) cycle. The other issue for pulsed oxygen concentrators which can be limiting is when a patient tries to take more breaths per minute than the unit is capable of producing. When this occurs, the oxygen user will either get a smaller pulse, a pulse with less oxygen, or no pulse at all. In a situation where the oxygen user exerts and become significantly out of breath, the unit may fail to meet the user's needs. With a nasal or oral flow temperature sensor in accordance with the present disclosure, we are able to get closer to the equivalent of continuous oxygen flow since the oxygen is delivered essentially immediately (i.e., generally within less than about 20 milliseconds, typically within 10-20 milliseconds of the onset of inhalation after the user begins to inhale air). Without the delay inherent in the pressure sensor method of triggering oxygen release as previously discussed, there is no need to push up the bolus amount to make up for the delay in delivery.

Also using onset of inhalation flow triggered pulse oxygen in accordance with the present disclosure, due to the increase in sensitivity in detecting onset of inspiration, the user does not have to think how he or she is breathing—the trigger senses onset of inspiration by a temperature drop through the flow sensor even when the patient is mouth breathing or while talking, walking and talking, or eating. It does not matter if the user has large nostrils or if the user is dozing in a chair, or sleeping. There is no required training—the user just places the cannula in his or her nostrils or mouth and experiences essentially synchronous oxygen delivery. As noted supra, conventional pressure flow-triggered pulse oxygen delivery has a noticeable delay in the "puff" of oxygen delivered, while onset of inspiration-flow-triggered oxygen delivery using temperature drop in accordance with the present disclosure has essentially no perceivable delay, giving it a more natural feel. It releases the oxygen essentially as the user is inhaling not after the user starts inhaling. Compared also to when using a conventional chest strain gauge to judge onset of inhalation, the flow sensor of the present disclosure triggered opening of the valve before any chest motion is detected! This improved synchronicity between onset of inhalation and oxygen delivery is more comfortable, more efficacious and more reliable, and since it actually performs what other types of conserving units only claim to do, will yield better patient compliance.

Additional uses of the present disclosure are in the diagnostic field of sleep disorders. Much attention has been directed toward sleep studies to confirm the diagnosis of sleep apnea, which is being diagnosed both in sleep labs and home sleep studies. The sensing and documentation of breathing during sleep can be enhanced by measuring inspiratory flow more accurately. Thus the same nasal flow temperature sensor which can trigger pulse oxygen delivery also can be adapted to efficiently measure breathing during diagnostic evaluations. Patients who have sleep apnea or periodic breathing and are only using oxygen supplementation also can now use pulsed oxygen delivery safely. This device can now allow patients who use C-PAP or Bi-PAP machines to take advantage of the efficiency benefits of pulsed oxygen delivery—delivering supplemental oxygen only during inspiration. This is an improvement over the current method of just adding oxygen to the hose traveling to the mask, which provides a most inefficient oxygen delivery system given the built-in mask venting as well as the inadvertent mask leaks which occur during the night.

Onset of inspiration-triggered oxygen delivery in accordance with the present disclosure also can free up traveling patients who are currently limited to 3 liters per min continuous flow rates. With portable concentrators, setting a pulse rate of 4-6+ liters per min while sleeping is just not reliable ("Critical Comparisons of the Clinical Performance of Oxygen-conserving Devices," Am. J. Respir. Crit. Care Med. 2010 May 15; 181(10): 1061-1071; Published online 2010 Feb. 4. doi: 10.1164/rccm.200910-1638OC PMCID: PMC2874449). These pulsed high flow devices claim to be able to oxygenate patients while sleeping, but most healthcare providers do not consider pulsed high flow devices to reliably deliver sufficient oxygen to sleeping patients.

Onset of inspiration triggered oxygen delivery in accordance with the present disclosure also can be adapted to "piggyback" onto hospital and clinic central liquid oxygen systems at the point of delivery, providing efficiency where none exists currently.

Figure 2:
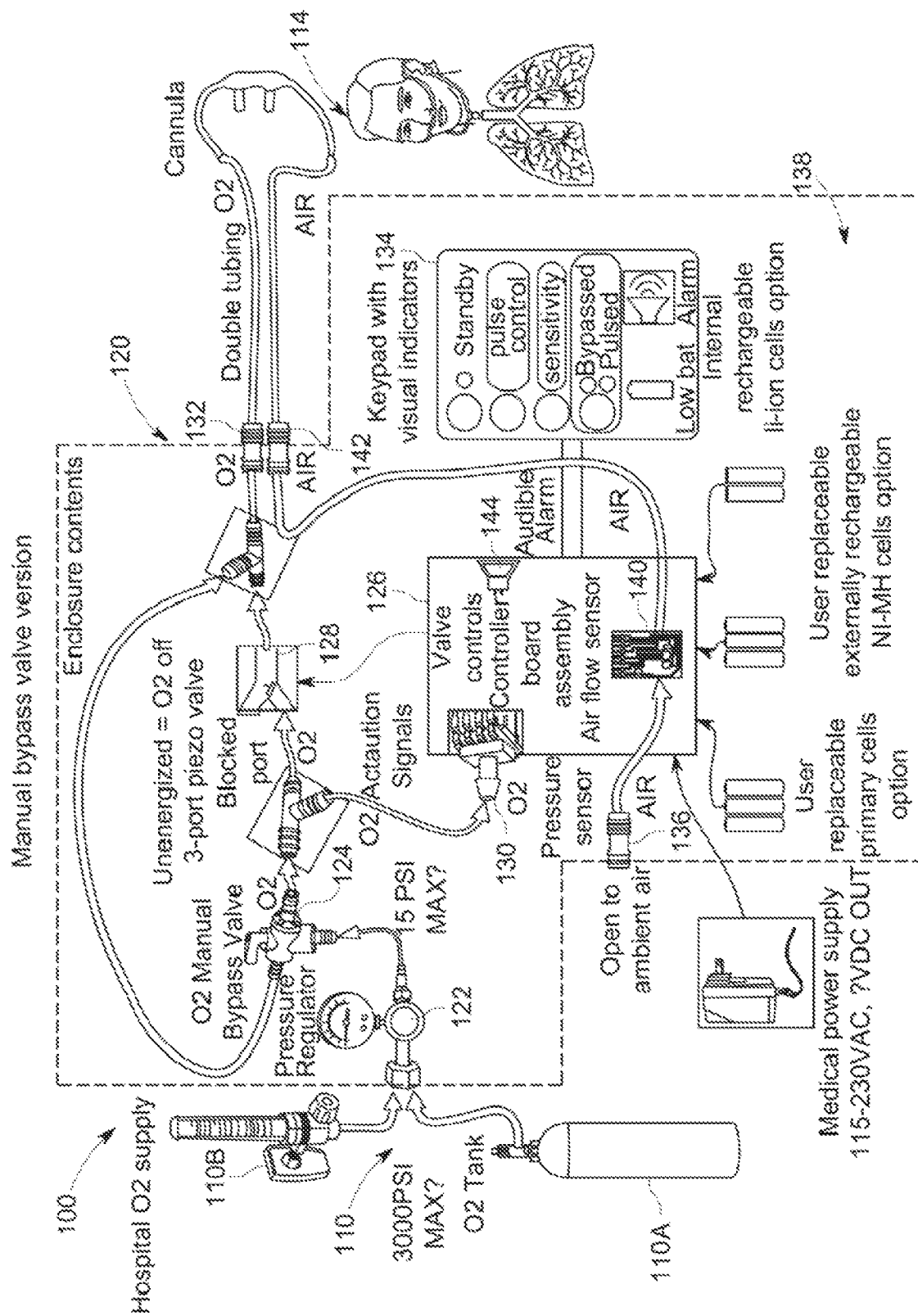
Figure 3:
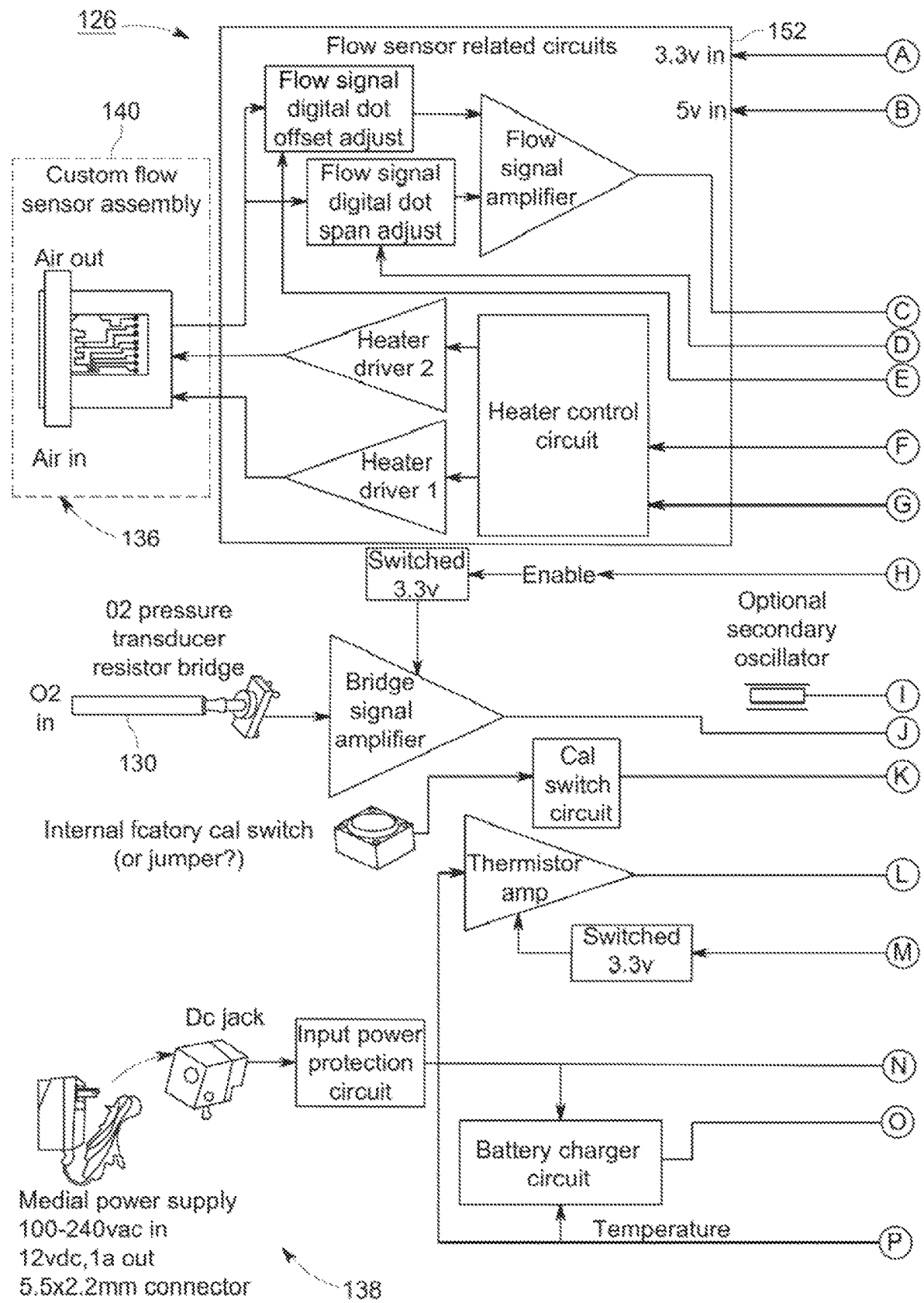
FIG. 3 is a block diagram of a remote sensor and control in accordance with a preferred embodiment of the present disclosure.
Figure 3:
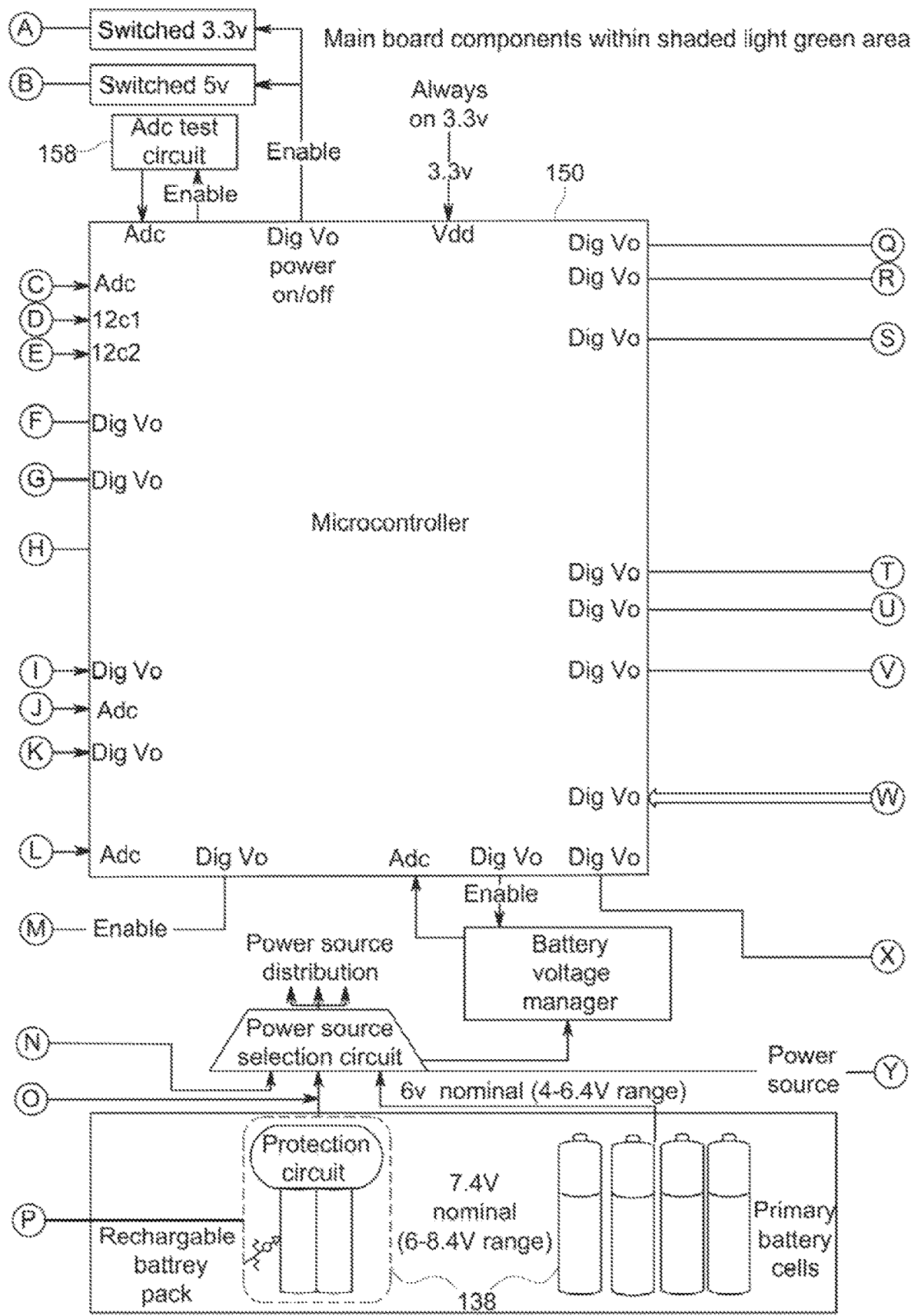
Figure 3:
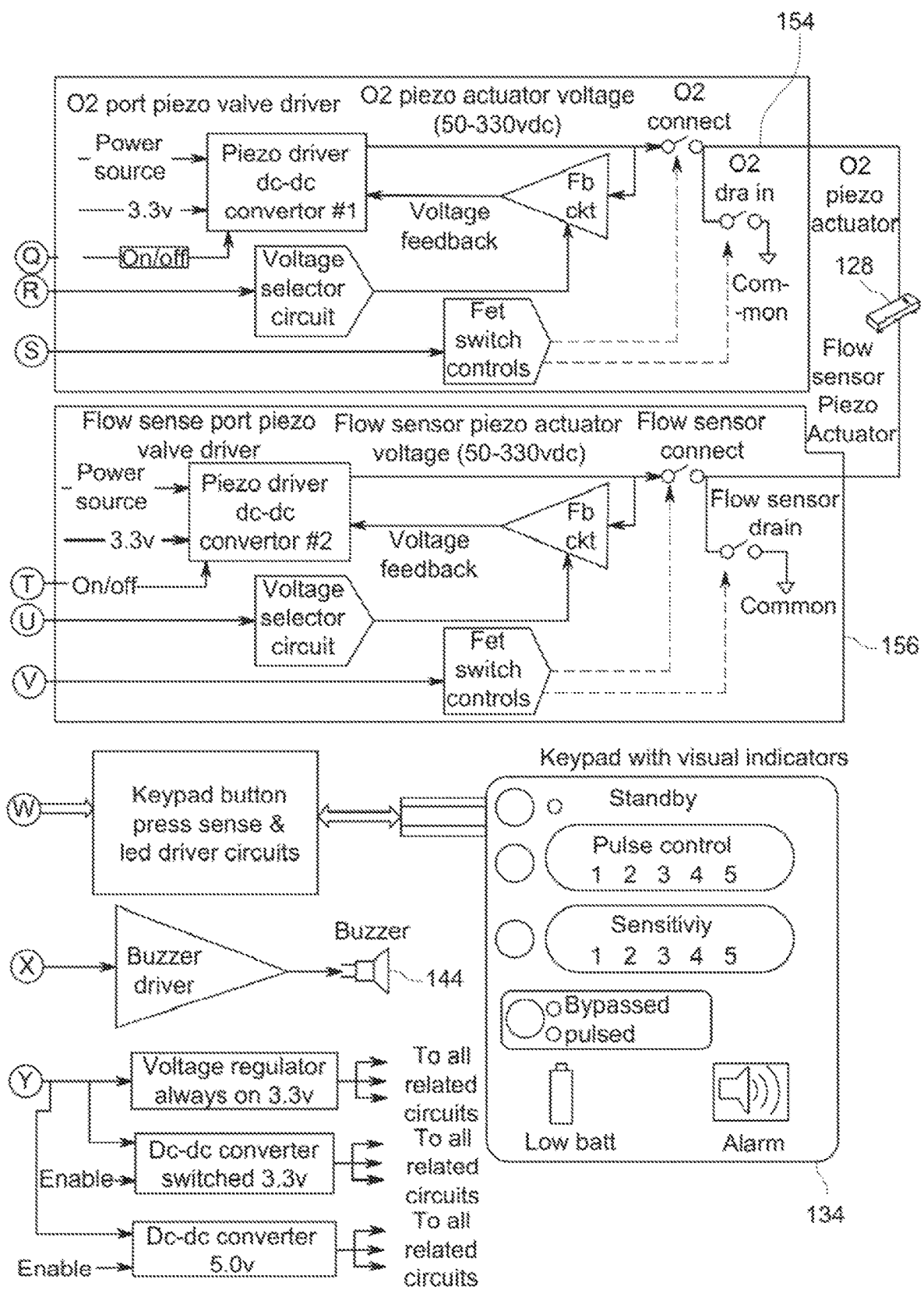

Referencing now to FIGS. 1-3 of the drawings, FIG. 1 is a block diagram illustrating the components of the enclosure of the fluid delivery system 100 in accordance with a first exemplary embodiment of the present disclosure. More particularly, FIG. 1 illustrates the fluid delivery system with a manual bypass valve configuration.

The system 100 includes an enclosure 120 which may be a housing or similar structure which contains the various components used for fluid delivery, such that a supply of oxygen (O2) 110 can be delivered to a patient 114. The oxygen supply 110 may include an oxygen tank 110A, a piped oxygen supply 110B from a hospital or other medical facility, or another device for supplying oxygen. Within the enclosure 120, the system 100 includes a pressure regulator 122 which is connectable to the oxygen supply 110 and regulates the pressure at which oxygen is introduced to the system 100. The oxygen supply 110 may be removably attachable to the system 100 using a connector of the pressure regulator 122. The pressure of the oxygen supply may be substantially high, such as up to 3,000 PSI in some situations, and on the outlet side of the pressure regulator 122, the pressure may be lowered to the desired PSI, such as 15 PSI in one example. Receiving the oxygen from the pressure regulator 122 is a manual bypass valve 124, which allows for manual control of oxygen delivery to the patient 114. Specifically, the manual bypass valve 124 may allow the user to select oxygen delivery along a first path, where pulsed oxygen delivery is controlled by the electronic controller 126, known as 'pulsed mode', or along a second path which substantially bypasses the controller 126 and delivers the oxygen directly or near-directly to the patient 114, known as 'bypass mode'.

When in pulsed mode, i.e., when the manual bypass valve 124 is positioned to deliver oxygen to the patient which is controlled by the controller 126, the oxygen is directed to a valve 128, which may be a 3-port piezo electric valve or another type. When the valve 128 is in an unenergized state, it blocks the flow of oxygen therethrough, and when energized or activated, it opens one or more of the valve ports to allow the flow of oxygen through it. The supply of oxygen to the valve 128 is also in fluid communication with an oxygen pressure sensor 130 which is connected to the controller 126, such that the pressure of the oxygen can be sensed. The output of valve 128 is connected to the oxygen output 132 of the system 100 which leads to the patient 114. As shown in FIG. 1, oxygen delivery to the patient may include various tubing with a nasal cannula 143 which can be positioned proximate to the patient's nose, however other delivery systems also may be used, including face masks, mouth pieces or the like.

The controller 126 also includes electronic control components, such as microcontrollers, circuits, input and output devices, or other components which control activation and use of the system 100, which are described in detail relative to FIG. 3. In general terms, the controller 126 is in communication with valve 128, the oxygen pressure sensor 130, an indicator device 134, an ambient air supply 136, and a power supply 138. The ambient air supply 136 may include a port in the enclosure 120 which intakes ambient air and passes it by an air flow sensor 140. Air flow sensor 140 is in communication with the nasal cannula 143 and provides the processor or microcontroller with a reading of the ambient air flow and senses onset of inspiration as well as discussed below. The output of the ambient air supply 136 may be delivered to the patient 114 using tubing and a cannula, mask, mouth piece or other delivery components, or via ambient air outlet 142 and dual lumen cannula as illustrated in FIG. 2.

The indicator device 134 may include a variety of indicator types, such as in one example, a keypad with visual indicators. Other types of indicators may also be used. The visual indicators of the indicator device 134 may include visual indicators for operations including standby, pulse control, sensitivity, bypassed or pulsed delivery, for power level, and for an alarm. Commonly, the indicator device 134 may be substantially integrated into the enclosure 120, but it also may be a fully or partially separate device. The power supply 138 may include one or more different electrical power supply devices such as a hardwired device, e.g., a 115/230 VAC supply, user-replaceable batteries, user-replaceable batteries which are capable of being recharged, or internal rechargeable batteries which may or may not be replaceable. Naturally, the power supply 138 may include combinations of these or other power sources to ensure continued operation of the system 100 in the event that one of the power sources fails. The controller 126 may include additional components, such as an audible alarm system 144 to provide an audible alarm to the patient or another user, as needed. Additional components of the controller 126 are discussed relative to FIG. 2.

In operation, the cannula or other delivery device is positioned proximate to the patient's 114 mouth or nose. The system 100 receives oxygen from the oxygen supply 110 and ambient air through the ambient air supply 136. When patient inhales, a negative pressure is applied to the cannula tubing which is received at the oxygen output 132 and/or the ambient air input 136. When in pulsed mode, the controller 126 is activated and control pulsed oxygen is delivered to the patient. Activation of the controller 126 causes the controller 126 to energize the piezoelectric valve 128, thereby opening a path for oxygen to flow from the oxygen supply 110, through the pressure regulator 122, through bypass valve 124, and to the patient 114. The controller 126 may control the specific flow of oxygen to the patient 114, such as, for example, by controlling the onset of flow of oxygen pulse length, pulse rate, or other pulse characteristic at which oxygen is allowed to pass through valve 128, or by controlling the sensitivity of activation or one or more components of the system 100. During control pulsed oxygen delivery, the patient 114 may continue to receive ambient air through the ambient air input 136.

The controller 126 may be activated manually such as with a button or switch, or more preferably in accordance with the present disclosure, automatically through a sensed signal indicative of onset of inspiration. In one example, the controller 126 may be activated by sensing a temperature change that results when the patient begins to inhale. In this example, a flow sensor in the form of a thermistor 140 positioned in the path of the ambient air supply 136 is heated to a temperature above ambient, typically 10 to 20° C. above ambient. When the user inhales, the in-line thermistor detects a drop in temperature resulting from the flow of ambient air past the heated thermistor 140. When this drop in temperature is detected, an activation signal is sent to the valve 128 to release oxygen. Alternatively, it is possible to heat the air in the path of the ambient air supply 136 which is located proximate to the thermistor 140 to a temperature above ambient. When the user inhales, a thermistor may be used to detect an increase in temperature of the ambient air flow supply as it passes by the thermistor 140, which in turn, can be used to send the activation signal. In a preferred embodiment, thermistor is configured to measure change in temperature in either direction, i.e., to measure a change in temperature on inhalation for triggering oxygen delivery, and to measure a change in temperature on exhalation, for triggering cessation of delivery of oxygen. Sensing the onset of exhalation also allows the system to deliver a single trigger for each inhalation. After sensing inhalation and triggering a pulse of fluid the system can prevent triggering again on the same inhalation by inhibiting any triggers until exhalation is sensed.

In order to protect the flow sensor from the high pressure oxygen flow valve 128 comprises dual actuator piezo valves 200, 202. Piezo valve 200 is connected inline between the supplemental oxygen source 110 and the flow sensor board 140, while piezo valve 202 is connected on one side to sensor board 140 and open on the other side to ambient air. Isolating the flow sensor from the high pressure oxygen flow permits the use of a highly sensitive flow sensor which in turn permits us to sense inhalation essentially immediately at onset, which in turn permits us to trigger a pulse of oxygen at the most opportune time, without waste. Prior art conservators which sense and deliver gas flow from the same line and are unable to sense inhalation essentially immediately at onset. Also, by isolating the flow sensor, we eliminate any contamination of flow from the users exhaust breath.

The description of the operation of the system 100 thus far is for when the system is in pulsed mode, i.e., where oxygen delivery is controlled by the electronic controller 126. Using the manual bypass valve 124, however, the user can change the system 100 from pulsed mode to bypass mode to deliver oxygen to the patient 114 directly. As shown in FIG. 1, in bypass mode, the supply of oxygen 110 from the pressure regulator 122 may pass through the manual bypass valve 124 and be directed to the oxygen outlet 132 directly or nearly directly, since the oxygen may pass through one or more dividing couplings. Thus, in bypass mode, the oxygen is delivered to the patient 114 without pulse control from the controller 126. Using the bypass valve 124, the user can control the desired mode of operation of the system 100 as needed, depending on the patient or the intended use of the system 100.

FIG. 3 is a block diagram illustrating an electrical block diagram of the controller 126 of the fluid delivery systems 100 and 102, of FIGS. 1-2, respectively, in accordance with a third exemplary embodiment of the present disclosure. As shown in FIG. 3, the controller 126 includes various controller circuitry and processing modules which are in communication with the components of the fluid delivery system. All components may be in communication with a microcontroller 150, which may receive signal and processing data from each of the components and control processing functions.

The microcontroller 150 is connected to the oxygen sensor 130 or oxygen transducer resistor bridge, whereby the signal from the oxygen sensor 130 is amplified with a bridge signal amplifier, and then input into the microcontroller 150 through an ADC connection. An optional secondary oscillator may be provided to the microcontroller 150. An internal factory CAL switch or jumper may be connected to the microcontroller 150 through a CAL switch circuit. The temperature of the ambient air supply 136, which is sensed by the thermistor 140, may be connected to the microcontroller 150 by a flow sensor circuit 152. Within the flow sensor circuit 152, a heater control and one or more heater drivers may be used to heat the thermistor 140 and/or the ambient supply surrounding it, and the flow signal from the thermistor 140 is received back in the flow sensor circuit 152. The signal may be processed by offset adjust and/or span adjust and then amplified before transmission to the microcontroller 150.

The piezoelectric valve 128 receives control signals from an oxygen port piezo valve driver 154 and a flow sense port piezo valve driver 156, which are connected to the microcontroller 150. The oxygen port piezo valve driver 154 has a piezo driver DC-DC converter which is connected to the power supply and an on/off signal, a voltage selector circuit, and FET switch controls. The flow sense port piezo valve driver 156 has a second piezo driver DC-DC converter, a voltage selector circuit, and FET switch controls. During operation of either driver 154, 156, a signal from the voltage selector circuit is provided to a FB circuit, which provides a voltage feedback to the piezo driver DC-DC converter. A signal from the microcontroller received at the FET switch controls is transmitted to the corresponding connect or drain switch for each driver 154, 156. The resulting signals from the oxygen switch of oxygen port driver 154 and the flow sensor switch of the flow sense driver 156 are transmitted to the piezoelectric valve 128 to control energization and actuation.

The indicator device 134 may be connected to the microcontroller 150 through one or more keypad button-press sense & LED driver circuits. Similarly, the audible alarm system 144 may be connected to the microcontroller 150 using a buzz driver. The power supply 138, including a hardwired power supply or battery power supply, may be connected to the microcontroller 150 using a power source selection, which controls power source distribution. Various voltage regulators and converters may be used to facility powering the various circuits and components of the system for fluid delivery, either directly, or through the microcontroller 150 as shown in FIG. 3. Additional power supply components may also be included, such as a power input protection circuit, charging circuits, a battery voltage monitor, or others. The microcontroller 150 also may have an ADC test circuit 158 connected thereto.

Figure 4:
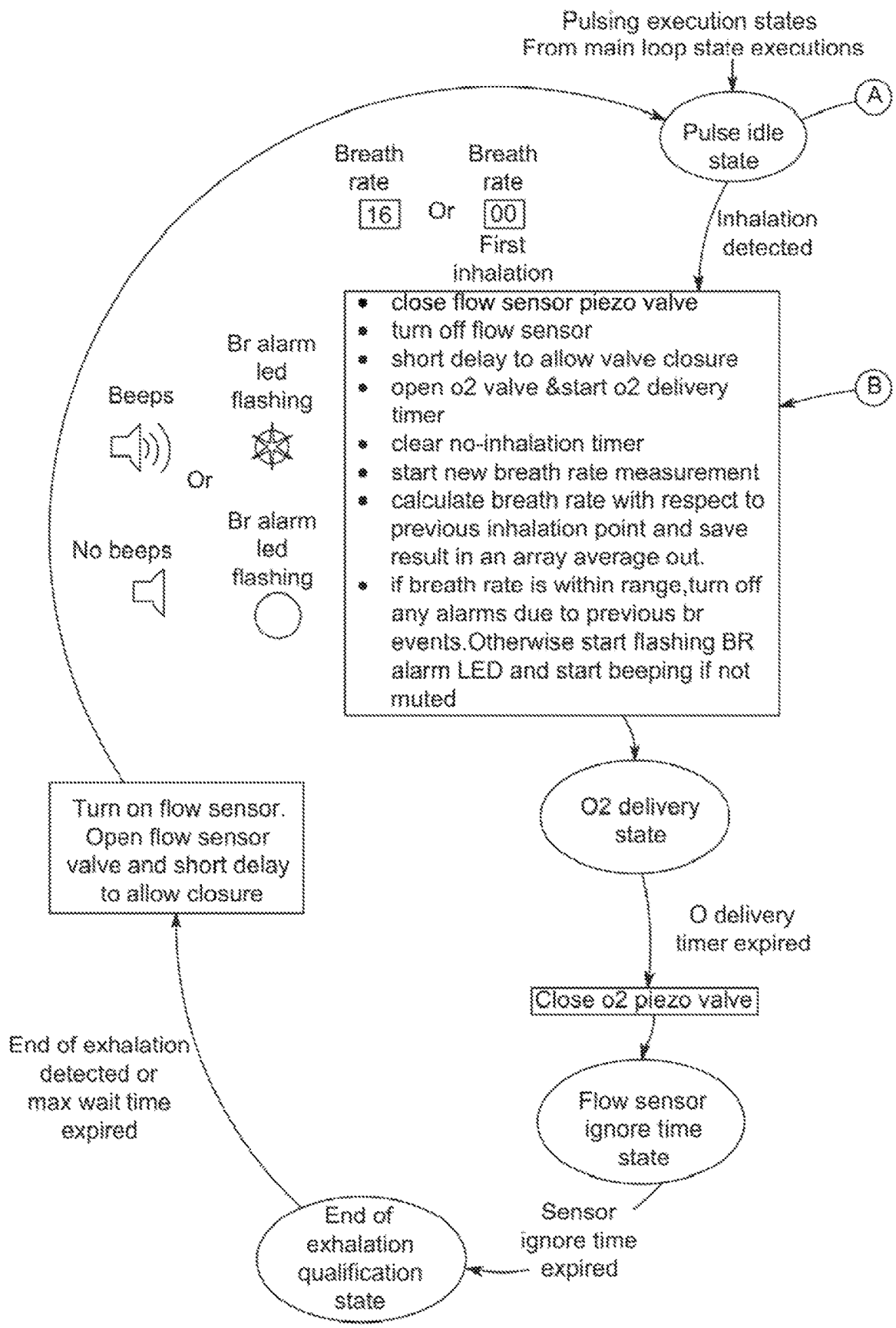
FIG. 4 schematically illustrates the triggering algorithm in accordance with a preferred embodiment of the present disclosure.
Figure 4:
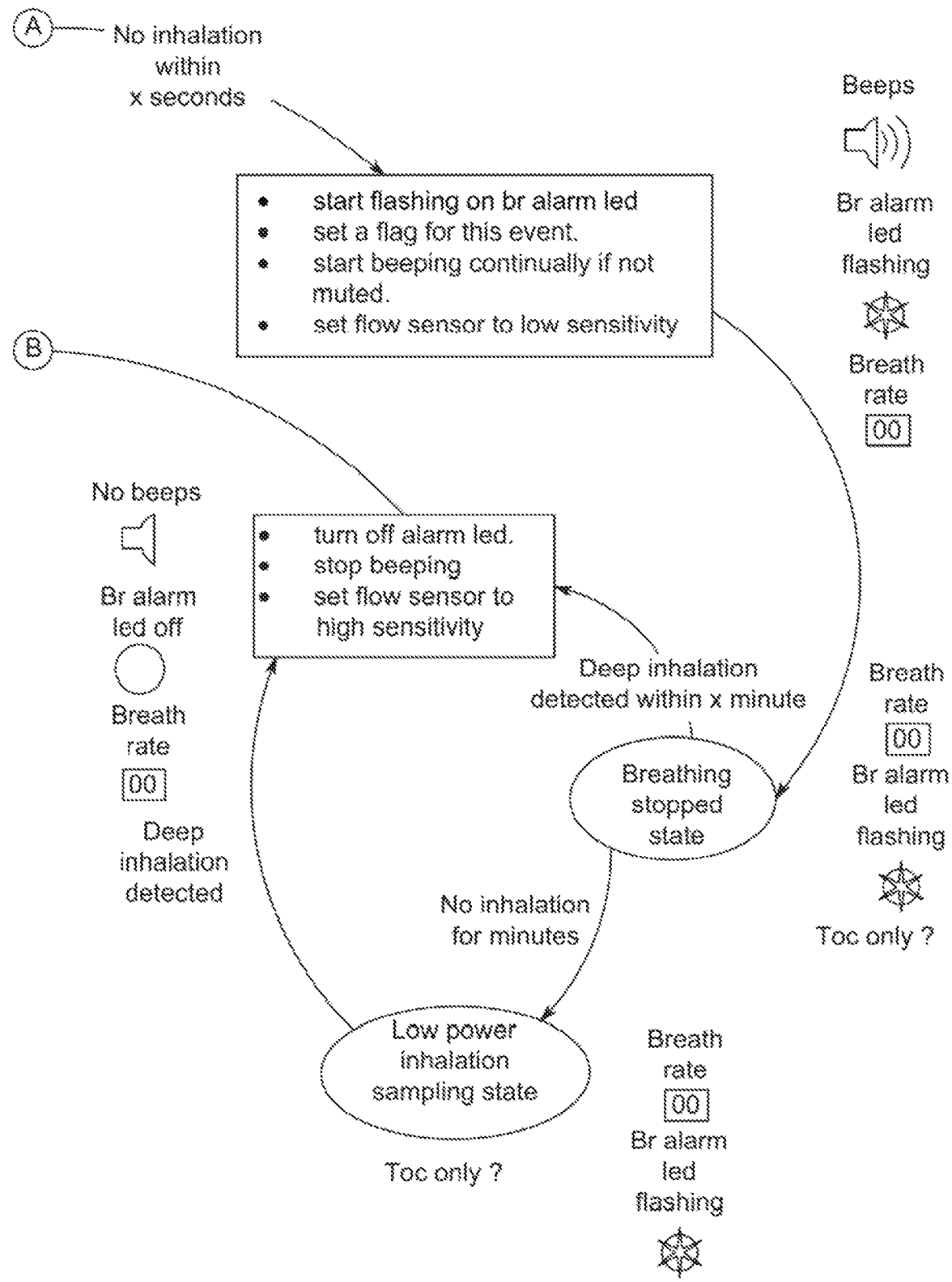

Further details of the present disclosure are found in FIG. 4 which is a schematic diagram illustrating the operation algorithm of a supplemental oxygen delivery system for the present disclosure and illustrates how after sensing inhalation and triggering a pulse of fluid, the system can prevent triggering again on the same inhalation by inhibiting any further triggers until exhalation is sensed.

FIG. 5 Table I which reports response times in triggering of supplemental oxygen flow following onset of inspiration of a patient in accordance with the present disclosure using a temperature sensor, compared with triggering of supplemental oxygen flow following onset of inspiration using the conventional pressure sensors, a Chad Lotus Therapeutic Oxygen Conserver. Model OM-700, and a SmartDose Oxygen Conserver, Model CTOX-MN02. In tests, a temperature sensor flow sensor in accordance with the present disclosure was found to be 40 times more sensitive than conventional state of the art pressure flow sensor.

Figure 6:
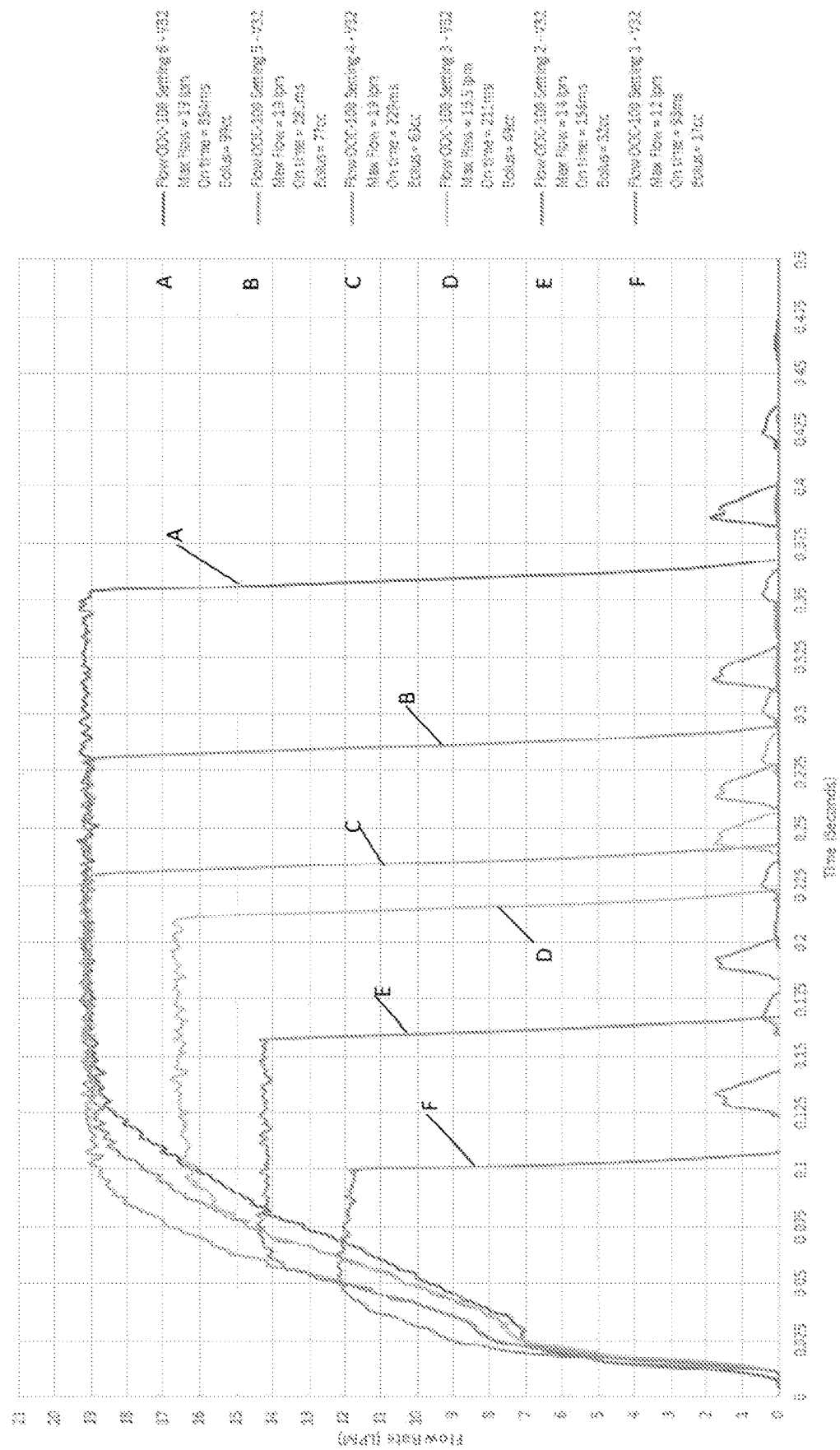
FIG. 6 is a flow chart of gas flow delivery of the present disclosure.
Figure 7:
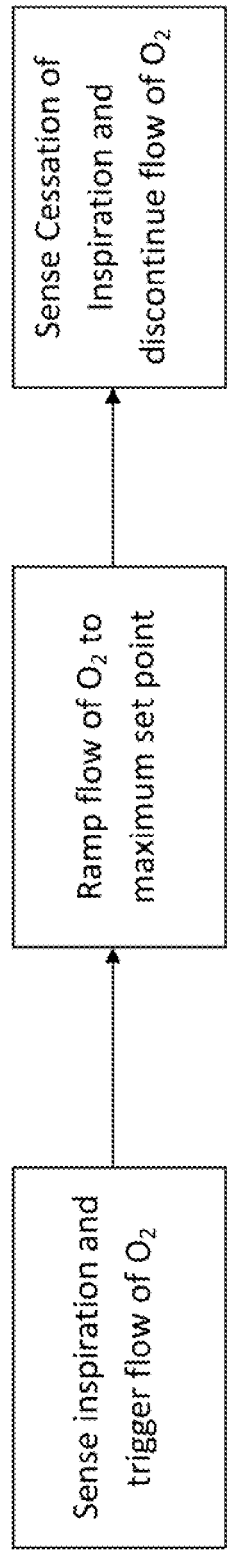
FIG. 7 is a block flow diagram depicting gas flow delivery according to the present disclosure.

FIG. 6 illustrates a flow chart for gas delivery in accordance with a preferred embodiment of the disclosure. More particularly, we have found that by ramping up delivery of supplemental oxygen flow from the sensed onset of inhalation, supplemental oxygen is better conserved, i.e., there is little or no loss blowing past the mask or cannula, and the user is much more comfortable. This is due to the fact that switching on the full metered flow of supplemental oxygen from a pressurized source as is done conventionally would result in flow of oxygen to the user at an initial rate far in excess than the user could tolerate. That is to say, due to the natural expansion of the lungs on breathing a user can't take in full target flow of supplemental oxygen fast enough for comfort and efficiency. Thus, rather than hit the wearer with full targeted flow of supplemental oxygen, upon detect of onset of inhalation, the flow of supplemental oxygen is ramped, essentially to coordinate with the breathing pattern of the user. Typically the delivery of supplemental oxygen is ramped from a starting flow of 15-40%, preferably 20-35%, more preferably 33% from triggering, to 100% target flow at maximum inspiratory capacity of the user, and is then turned off and paused as or prior to the time the user begins to exhale. By way of example, assuming a target flow of 16 liters of oxygen per minute, the flow of oxygen upon onset of inspiration initially may be set to 5 or 6 liters per minute, and ramped to 16 liters per minute coordinated with the user's inspiration, and then shut off as inspiration ceases or slows as sensed by the flow sensors. This is illustrated in FIG. 7.

Although the present disclosure has been described in detail with reference to certain embodiments, one skilled in the art will appreciate that the present disclosure can be practiced by other than the described embodiments, which have been presented for purposes of illustration and not of limitation. For example, the above described system may be plugged into a conventional fixed flow regulator, or to a conventional hospital wall unit regulator, and convert same to a "smart regulator". The system also may be built into or adapted as an add-on feature to a C-PAP mask. The system also may be used for controlling delivery of therapeutic gas such as nitric oxide or anesthetic gas, or for regulating flow of supplemental oxygen or breathing gases for mountaineering and scuba applications, for fire and rescue protective gear, space suit applications and the like which may employ sealed helmets rather than nasal or oral cannula, or masks. Thus, as used herein nasal cannula and oral cannula are intended to also include masks, sealed helmets, and the like. Still other changes are possible. Therefore, the scope of the appended claims should not be limited to the description of the embodiments contained herein.

I claim:

1. A fluid delivery system for controlling delivery of a fluid to a human or animal comprising:
   at least one source of said fluid;
   at least one valve assembly coupled to said at least one source of said fluid, wherein the at least one valve assembly is configured to allow flow of said fluid from the at least one source during said human or animal inspiration;
   an outlet end comprising a nasal cannula, an oral cannula, a mask or a helmet in fluid communication with the at least one valve assembly;
   an electronic MEMS flow sensor for triggering fluid delivery in response to said human or animal inspiration, and
   a heater configured to heat the flow sensor or fluid upstream of the flow sensor to above ambient,
   wherein the flow sensor is in fluid communication with and upstream the nasal cannula, the oral cannula, the mask or the helmet and comprises a thermal sensor configured to detect a change in temperature indicative of onset of inspiration by said human or animal, within less than about 20 milliseconds of said onset of inspiration, and
   wherein the at least one valve assembly is configured to commence fluid flow delivery from the triggering beginning at inspiration of the human or animal, and to ramp fluid flow delivery from a starting flow of 15-40% from the triggering beginning at inspiration of the human or animal and ramp to 100% fluid flow delivery and then turn off or pause fluid flow delivery as or prior to a time the human or animal begins to exhale to coordinate with a breathing pattern of the human or animal.

2. The fluid delivery system of claim 1, further comprising a power source configured to operate the at least one valve assembly.

3. The fluid delivery system of claim 1, wherein the flow sensor is located in or adjacent the nasal cannula or oral cannula, mask or helmet or is located in tubing connective the nasal cannula, mask or helmet or oral cannula and the at least one source of said fluid.

4. The fluid delivery system of claim 1, wherein the fluid delivered comprises supplemental oxygen, a therapeutic gas or an anesthetic gas.

5. The fluid delivery system of claim 1, further comprising electronic circuitry for controlling the at least one valve assembly based on signals from the flow sensor, and
wherein the electronic circuitry preferably comprises a trigger mechanism for actuating the release of said fluid through said at least one valve assembly.

6. The fluid delivery system of claim 1, wherein the at least one valve assembly is configured to ramp fluid flow delivery from a starting flow of 20-35% from the triggering to 100% flow at inspiratory capacity of the human or animal.

7. The fluid delivery system of claim 1, wherein the thermal sensor is configured to detect the onset of inspiration and the onset of exhalation by a directional change of temperature, and wherein the system optionally includes heaters located downstream of said temperature sensor.

8. The fluid delivery system of claim 1, wherein the flow sensor is isolated from the at least one source of said fluid by a piezo actuator valve.

9. An apparatus for conserving fluid being delivered from a fluid supply to a human or animal comprising:
a fluid conserver controller connected between the fluid supply and a nasal cannula, an oral cannula, a mask or a helmet wherein said controller comprises at least one valve triggered selectively to deliver said fluid to the nasal or oral cannula, mask or helmet;
an electronic MEMS flow sensor configured to sense inspiration by human or animal;
a heater configured to heat the flow sensor or the fluid upstream of the flow sensor to above ambient;
a trigger mechanism, communicating with said flow sensor for actuating the fluid conserver controller, wherein the flow sensor is in fluid communication with the nasal cannula, the oral cannula, the mask or the helmet, and includes a thermal sensor configured to detect a change in temperature indicative of onset of said inspiration by said human or animal, within less than about 20 milliseconds of said onset of inspiration,
wherein the at least one valve assembly is configured to commence fluid flow delivery from the triggering beginning at inspiration of the human or animal, and to ramp fluid flow delivery from a starting flow of 15-40% from the triggering beginning at inspiration of the human or animal and ramp to 100% fluid flow delivery and then turn off or pause fluid flow delivery as or prior to a time the human or animal begins to exhale to coordinate with a breathing pattern of the human or animal.

10. The apparatus of claim 9, wherein said flow sensor and said trigger mechanism are remote from one another, and wherein said flow sensor and said trigger mechanism communicate either by wire or wirelessly.

11. The apparatus of claim 9, wherein the fluid supply comprises oxygen, a therapeutic gas or an anesthetic gas.

12. The apparatus of claim 9, further comprising electric circuitry for controlling the at least one valve assembly based on signals from the flow sensor.

13. The apparatus of claim 9, wherein the at least one valve assembly is configured to ramp fluid flow delivery from a starting flow of 20-35% from the triggering to 100% flow at inspiratory capacity of the human or animal.

14. The apparatus of claim 9, wherein the temperature sensor is configured to detect the onset of inspiration and the onset of exhalation by a directional change of temperature, and wherein the system optionally includes heaters located downstream of said temperature sensor.

15. The apparatus of claim 9, wherein the flow sensor is isolated from the fluid supply by a piezo actuator valve.

16. A method for conserving delivery of a fluid from a fluid source to a patient, comprising the steps of:
providing a valve in communication with said fluid source and a nasal cannula, an oral cannula, a mask or a helmet worn by the patient;
providing an electronic MEMS flow sensor in fluid communication with and upstream of the nasal cannula, the oral cannula, the mask or the helmet;
heating the flow sensor or the fluid upstream of the flow sensor, and
sensing, with the flow sensor in fluid communication with the nasal cannula, the oral cannula, the mask or the helmet, onset of inspiration by detecting a change in temperature of the fluid through the nasal cannula, the oral cannula, the mask or the helmet within less than about 20 milliseconds, of said onset of inspiration, wherein the flow sensor comprises a thermal sensor, and
triggering the valve, in response to the sensed onset of inspiration to release said fluid from the fluid source for delivery to the patient via the nasal cannula, the oral nasal cannula, the mask or the helmet,
wherein the at least one valve assembly is configured to commence fluid flow delivery from the triggering beginning at inspiration of the human or animal, and ramp fluid flow delivery from a starting flow of 15-40% from the triggering beginning at the inspiration of the human or animal and ramp to 100% fluid flow delivery and then turn off or pause fluid flow delivery as or prior to a time the human or animal begins to exhale to coordinate with a breathing pattern of the human or animal.

17. The method of claim 16, wherein the fluid comprises oxygen, a therapeutic gas or an anesthetic gas, and optionally further comprising heating the flow sensor or the fluid upstream of the flow sensor to above ambient.

18. The method of claim 16, wherein the flow sensor comprises a temperature sensor configured to detect the onset of inspiration and onset of exhalation by directional change of temperature.

19. The method of claim 16, including the step of isolating the flow sensor from the fluid source while sensing onset of inspiration.

20. The method of claim 16, wherein the at least one valve assembly is configured to ramp fluid flow delivery from a starting flow of 20-35% from the triggering to 100% flow of a target flow rate.

21. The method of claim 16, wherein the fluid flow is ramped to coordinate with a breathing pattern of the human or animal.

22. The method of claim 16, wherein the at least one valve assembly is configured to ramp fluid flow delivery from a starting flow of 33% from the triggering to 100% flow of a target flow rate.

* * * * *